(12) United States Patent
Sugai

(10) Patent No.: US 11,833,322 B2
(45) Date of Patent: Dec. 5, 2023

(54) DRUG SOLUTION ADMINISTRATION METHOD

(71) Applicant: SEIKO EPSON CORPORATION, Tokyo (JP)

(72) Inventor: Keigo Sugai, Chino (JP)

(73) Assignee: Seiko Epson Corporation, Tokyo (JP)

( * ) Notice: Subject to any disclaimer, the term of this patent is extended or adjusted under 35 U.S.C. 154(b) by 321 days.

(21) Appl. No.: 17/104,685

(22) Filed: Nov. 25, 2020

(65) Prior Publication Data
US 2021/0162190 A1 Jun. 3, 2021

(30) Foreign Application Priority Data
Nov. 28, 2019 (JP) .................. 2019-215079

(51) Int. Cl.
*A61M 37/00* (2006.01)
*A61M 5/46* (2006.01)

(52) U.S. Cl.
CPC .............. *A61M 37/00* (2013.01); *A61M 5/46* (2013.01)

(58) Field of Classification Search
CPC .................... A61M 37/00; A61M 5/46; A61M 2039/0205; A61M 5/3007; A61M 5/30
See application file for complete search history.

(56) References Cited

U.S. PATENT DOCUMENTS

2014/0200511 A1*  7/2014  Boyden ................ A61K 9/1611
                                                              606/213

FOREIGN PATENT DOCUMENTS

JP        2000-185106 A     7/2000

\* cited by examiner

*Primary Examiner* — Lauren P Farrar
*Assistant Examiner* — Hamza A Darb
(74) *Attorney, Agent, or Firm* — WORKMAN NYDEGGER

(57) ABSTRACT

A drug solution administration method using an inkjet device including an inkjet head that ejects a drug solution, and a controller that controls the ejection of the drug solution from the inkjet head, wherein the drug solution is made to pierce a target site and is administered to the target site by ejecting the drug solution from the inkjet head so that a diameter of the drug solution when it is ejected from the inkjet head is 20 μm or more and 200 μm or less and an ejection rate of the drug solution when it is ejected from the inkjet head is 30 m/s or more under control of the controller.

9 Claims, 7 Drawing Sheets

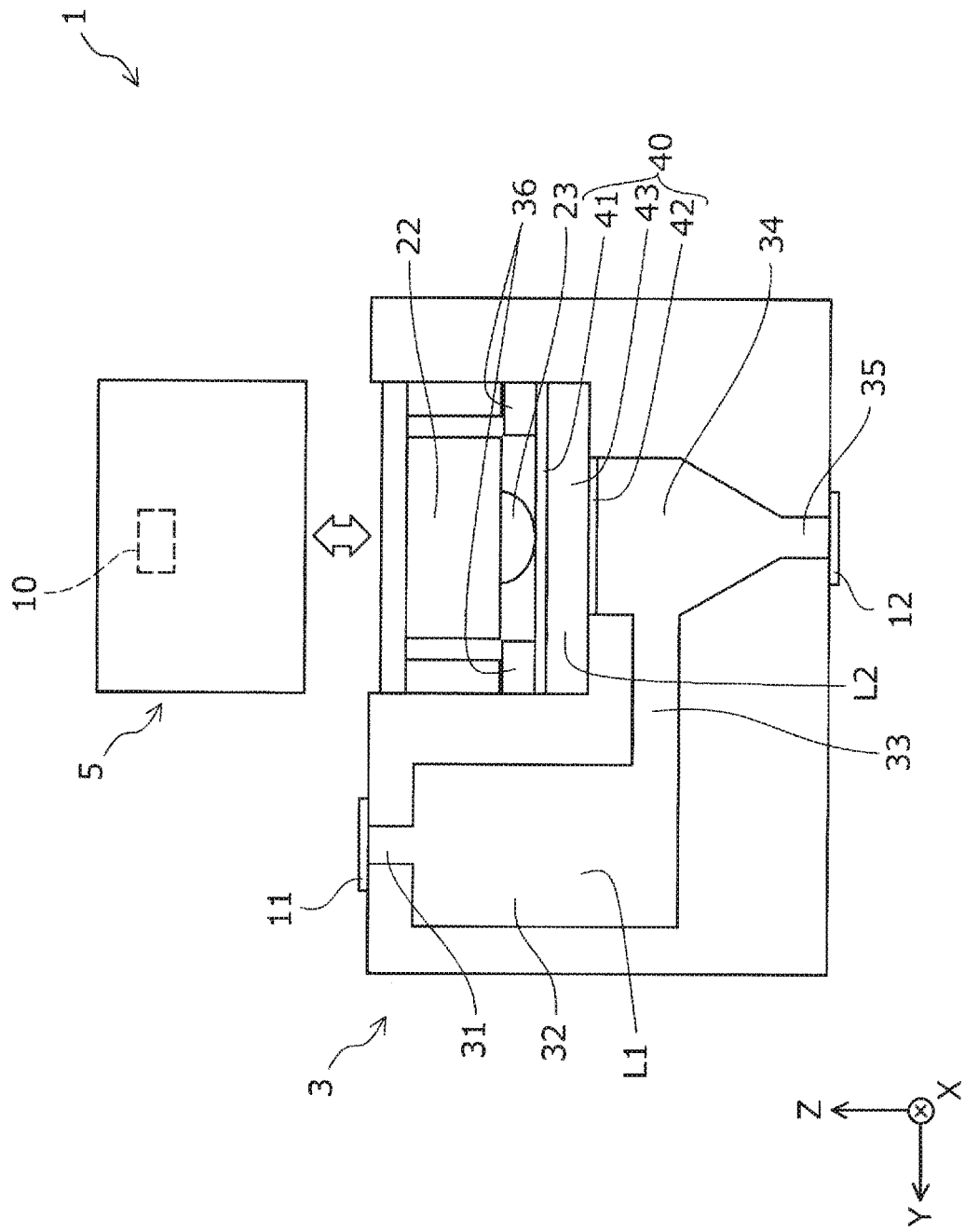

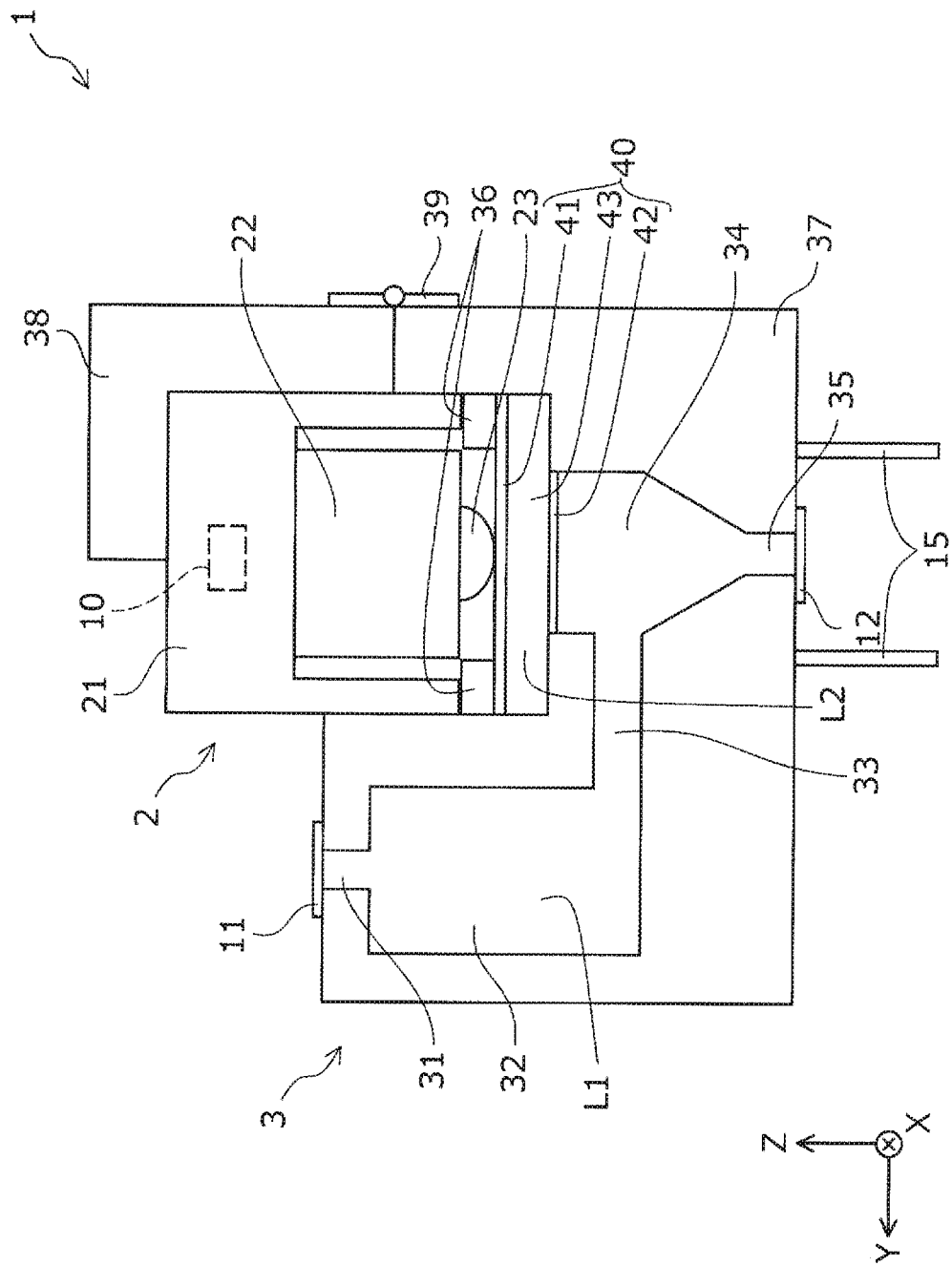

DRUG SOLUTION ADMINISTRATION METHOD

The present application is based on, and claims priority from JP Application Serial Number 2019-215079, filed on Nov. 28, 2019, the disclosure of which is hereby incorporated by reference herein in its entirety.

BACKGROUND

1. Technical Field

The present disclosure relates to a drug solution administration method.

2. Related Art

Heretofore, various methods for administering a drug solution to a target site such as an affected area have been used. As a representative method, an injection method for administering a drug solution inside a target site using a syringe and an injection needle is exemplified. Further, as disclosed in JP-A-2000-185106 (Patent Document 1), a method for administering a drug solution by ejecting a drug solution to a target site using an inkjet ejection device is also disclosed.

However, the injection method for administering a drug solution to a target site using a syringe and an injection needle sometimes causes pain to a patient, and also has an adverse effect that the patient may contract an infectious disease, or the like. Further, by a method for ejecting a drug solution to a target site using an inkjet ejection device in a related art as disclosed in Patent Document 1, the drug solution sometimes does not sufficiently penetrate inside from the surface of the target site depending on the type of the drug solution to be used.

SUMMARY

A drug solution administration method according to the present disclosure for solving the above problem is a drug solution administration method using an inkjet device including an inkjet head that ejects a drug solution, and a controller that controls the ejection of the drug solution from the inkjet head, wherein the drug solution is made to pierce a target site and is administered to the target site by ejecting the drug solution from the inkjet head so that a diameter of the drug solution when it is ejected from the inkjet head is 20 μm or more and 200 μm or less and an ejection rate of the drug solution when it is ejected from the inkjet head is 30 m/s or more under control of the controller.

BRIEF DESCRIPTION OF THE DRAWINGS

FIG. 6 is a schematic view showing a drug solution administration unit of a second embodiment capable of implementing a drug solution administration method according to the present disclosure, and is a view showing a state where a power supply unit is detached from a body portion.

FIG. 7 is a schematic view showing a drug solution administration unit of a third embodiment capable of implementing a drug solution administration method according to the present disclosure, and is a view showing a state where an actuator unit is set in a body portion.

DESCRIPTION OF EXEMPLARY EMBODIMENTS

Figure 1:
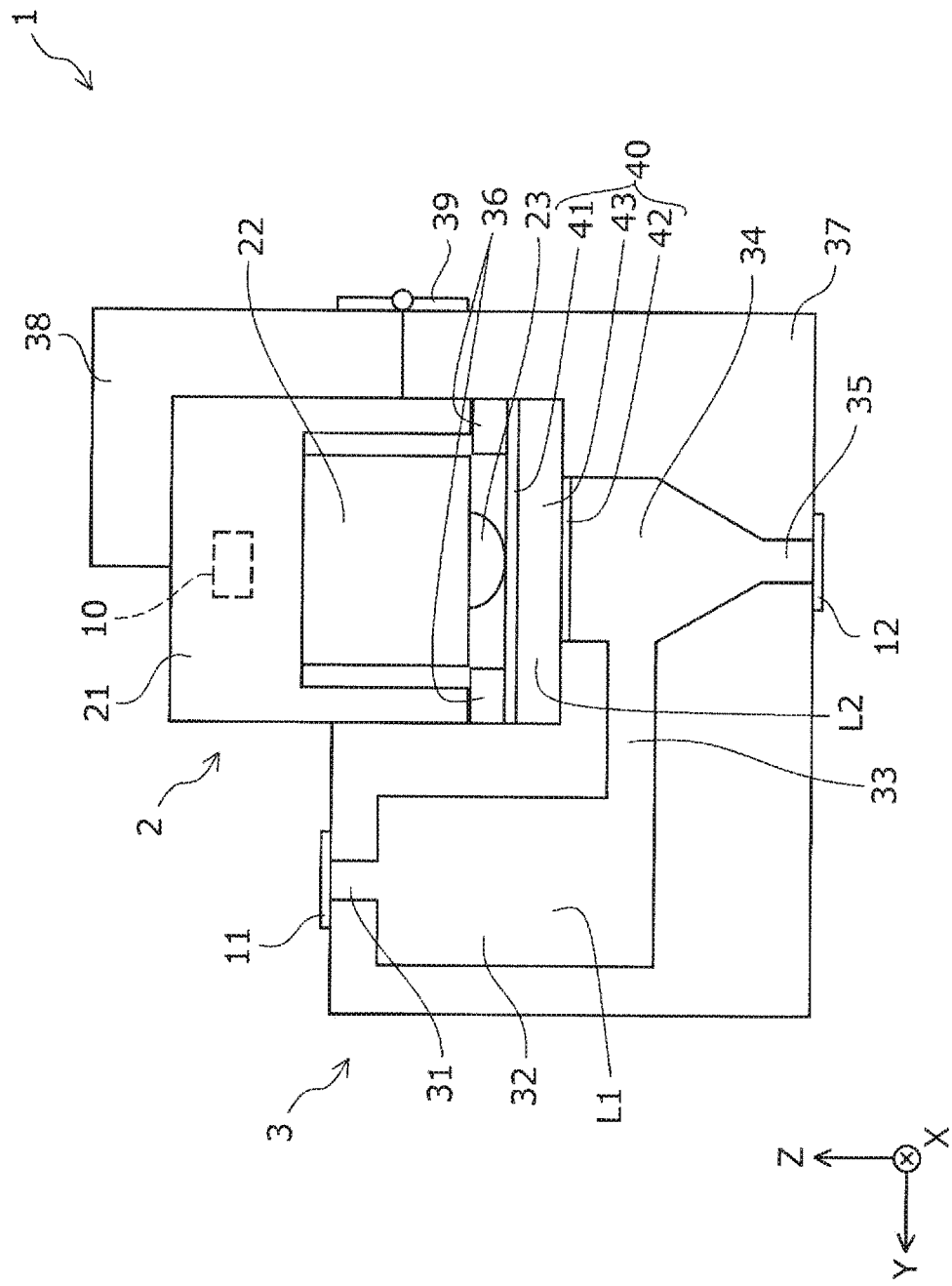
FIG. 1 is a schematic view showing a drug solution administration unit of a first embodiment capable of implementing a drug solution administration method according to the present disclosure, and is a view showing a state where an actuator unit is set in a body portion.

First, the present disclosure will be schematically described.

A drug solution administration method according to a first aspect of the present disclosure for solving the above problem is a drug solution administration method using an inkjet device including an inkjet head that ejects a drug solution, and a controller that controls the ejection of the drug solution from the inkjet head, wherein the drug solution is made to pierce a target site and is administered to the target site by ejecting the drug solution from the inkjet head so that a diameter of the drug solution when it is ejected from the inkjet head is 20 μm or more and 200 μm or less and an ejection rate of the drug solution when it is ejected from the inkjet head is 30 m/s or more under control of the controller.

According to this aspect, the drug solution is ejected so that the diameter is 20 μm or more and 200 μm or less and the ejection rate is 30 m/s or more. By administering the drug solution to the target site under such conditions, the drug solution can be administered while piercing the surface of the target site without causing a patient to feel pain, and the drug solution can be made to sufficiently penetrate into the target site. Further, by ejecting the drug solution from the inkjet head, the drug solution can be administered to the target site without bringing the other constituent members such as a needle into contact with the target site, and thus, the adverse effect can also be suppressed.

In the drug solution administration method according to a second aspect of the present disclosure, in the first aspect, the inkjet device includes an ejection rate measurement unit for the drug solution, and the administration of the drug solution is performed after measuring the ejection rate of the drug solution.

According to this aspect, the drug solution can be administered after measuring the ejection rate. The dose is sometimes restricted according to the type of the drug solution to be used, however, by adjusting the conditions so that the drug solution can pierce the target site, an accurate amount of the drug solution can be administered.

In the drug solution administration method according to a third aspect of the present disclosure, in the first or second aspect, the drug solution is administered while adjusting a penetration depth of the drug solution into the target site by changing the number of times of ejection of the drug solution at the same position of the target site under the control of the controller.

A preferred penetration depth of the drug solution into the target site varies depending on the state of the target site or the drug solution to be used. If the number of times of ejection of the drug solution at the same position of the target site is increased, the penetration depth of the drug solution into the target site is increased, however, according to this aspect, the drug solution can be administered while adjusting the penetration depth of the drug solution into the target site by a simple method in which the number of times of ejection of the drug solution at the same position of the target site is changed.

In the drug solution administration method according to a fourth aspect of the present disclosure, in any one of the first to third aspects, the inkjet device includes a moving mechanism for changing the position of the inkjet head, and in the administration of the drug solution, the drug solution is administered while changing the position of the inkjet head by the moving mechanism.

According to this aspect, the drug solution can be administered while changing the position of the inkjet head by the moving mechanism. Therefore, when the target site is located over a wide area, or the like, the drug solution can be easily administered at a preferred position.

In the drug solution administration method according to a fifth aspect of the present disclosure, in any one of the first to fourth aspects, the inkjet head is configured to be able to eject the drug solution with a plurality of ejection diameters under the control of the controller, and the drug solution is administered while adjusting an application range of the drug solution to the local target site by changing the ejection diameter of the drug solution under the control of the controller.

A preferred application range of the drug solution to the local target site varies depending on the state of the target site or the drug solution to be used. According to this aspect, the drug solution can be administered while adjusting the application range of the drug solution to the local target site by narrowing the ejection diameter of the drug solution.

In the drug solution administration method according to a sixth aspect of the present disclosure, in any one of the first to fifth aspects, the inkjet head is configured to be able to eject the drug solution at a plurality of ejection rates under the control of the controller, and the drug solution is administered while adjusting a penetration depth of the drug solution into the target site by changing the ejection rate of the drug solution under the control of the controller.

A preferred penetration depth of the drug solution into the target site varies depending on the state of the target site or the drug solution to be used. By increasing the ejection rate of the drug solution, the penetration depth of the drug solution into the target site is increased, however, according to this aspect, the drug solution can be administered while adjusting the penetration depth of the drug solution into the target site by changing the ejection rate of the drug solution.

In the drug solution administration method according to a seventh aspect of the present disclosure, in any one of the first to sixth aspects, the inkjet device includes an ejection distance specifying unit that specifies an ejection distance of the drug solution, which is a distance from the inkjet head to the target site, and the administration of the drug solution is performed within a range where the ejection distance is 5 mm or more and 20 mm or less by specifying the ejection distance by the ejection distance specifying unit.

If the ejection distance is too short, the drug solution may bounce back to the inkjet head to contaminate the inkjet head and make it unhygienic, and if the ejection distance is too long, it may become difficult for the drug solution to reach the target site at a desired ejection rate. According to this aspect, the administration of the drug solution is performed within a range where the ejection distance is 5 mm or more and 20 mm or less, and therefore, the inkjet head can be prevented from being contaminated and becoming unhygienic or the drug solution can be prevented from not reaching the target site at a desired ejection rate.

In the drug solution administration method according to an eighth aspect of the present disclosure, in any one of the first to seventh aspects, the inkjet head has an ejection port for ejecting the drug solution, a pressure chamber that communicates with the ejection port, an actuator that is displaced in a pressing direction and in an opposite direction to the pressing direction, and a displacement magnification mechanism for magnifying an amount of displacement and transmitting the displacement of the actuator to the pressure chamber.

It is difficult to eject a drug solution so that the ejection rate is 30 m/s or more using a general inkjet head. According to this aspect, the pressure chamber can be pressed with a larger amount of displacement than an amount of displacement of the actuator due to the displacement magnification mechanism, and therefore, the drug solution can be ejected so that the ejection rate is 30 m/s or more.

In the drug solution administration method according to a ninth aspect of the present disclosure, in the eighth aspect, the displacement magnification mechanism includes a liquid chamber in which a liquid is enclosed, a first wall portion that constitutes a part of a wall face of the liquid chamber, and that is displaced according to the displacement of the actuator so as to apply a pressure to the liquid, and a second wall portion that constitutes a part of a wall face of the liquid chamber, that has a smaller area facing the liquid than the area of the first wall portion facing the liquid, and that is displaced in the pressing direction in a state where an elastic force acting in the opposite direction is generated by a pressure of the liquid when a pressure is applied to the liquid by the displacement of the first wall portion.

According to this aspect, by adopting a configuration in which the liquid chamber having the first wall portion and the second wall portion is provided, a high-precision displacement magnification mechanism can be constituted. Then, by the high-precision displacement magnification mechanism, the drug solution can be ejected so that the ejection rate is 30 m/s or more with high precision.

In the drug solution administration method according to a tenth aspect of the present disclosure, in the eighth or ninth aspect, under the control of the controller, a surface of the drug solution formed at the ejection port is drawn toward the inside of the pressure chamber so as to form a recessed shape by displacing the actuator in the opposite direction, and a columnar shape protruding toward the outside of the pressure chamber is formed at a central portion when viewed from the ejection direction of the drug solution at the surface in the recessed shape and also the drug solution in the columnar shape is ejected by displacing the actuator in the pressing direction.

According to this aspect, the drug solution can be ejected so that the ejection rate is 30 m/s or more with high precision by displacing the actuator so as to once recess the surface of the drug solution formed at the ejection port, and thereafter form a columnar shape at a central portion of the recessed portion. Further, when the drug solution is ejected in a spherical shape, it is difficult to visually confirm whether or not the drug solution is ejected, however, by ejecting the drug solution in a columnar shape, it is possible to visually confirm whether or not the drug solution is ejected.

Hereinafter, embodiments according to the present disclosure will be described with reference to the accompanying drawings. Note that the following drawings are all schematic views, and some constituent members are omitted or shown in a simplified manner. Further, in the respective drawings, an X-axis direction is a horizontal direction, a Y-axis direction is a horizontal direction and also a direction orthogonal to the X-axis direction, and a Z-axis direction is a vertical direction.

First Embodiment

First, the entire configuration of a drug solution administration unit 1 that is an embodiment capable of implementing a drug solution administration method according to the present disclosure will be described with reference to FIGS. 1 to 4. As shown in FIGS. 1 to 4, the drug solution administration unit 1 of this embodiment has an actuator unit 2 and a body unit 3.

The actuator unit 2 includes a controller 10, an actuator holder 21, an actuator 22, and an abutment portion 23 other than a power supply (not shown). The actuator 22 is displaced along the Z-axis direction under the control of the controller 10. That is, by driving the actuator 22 under the control of the controller 10, the abutment portion 23 changes the position along the Z-axis direction with respect to the actuator holder 21. The drug solution administration unit 1 of this embodiment includes the controller 10 in the actuator unit 2, but may be configured to include the controller 10 in the body unit 3.

The body unit 3 includes an inlet port 31 for a drug solution L1, a drug solution chamber 32 that communicates with the inlet port 31, a passage 33 that communicates with the drug solution chamber 32, a pressure chamber 34 that communicates with the passage 33, and an ejection port 35 that communicates with the pressure chamber 34. The members from the inlet port 31 to the ejection port 35 constitute a storage portion for the drug solution L1. Further, the body unit 3 includes a mounting portion 37 on which the actuator unit 2 is mounted, and a pivot portion 38 that is coupled to the mounting portion 37 through a hinge 39 and can be pivoted by pivoting the hinge 39, which is easy to understand by comparing FIG. 1 and FIG. 2. The actuator unit 2 can be attached to and detached from the mounting portion 37 by pivoting the pivot portion 38 around the hinge 39 and moving the actuator unit 2 in the arrow direction in FIG. 2. In the drug solution chamber 32, a urethane foam for keeping the storage portion for the drug solution L1 at a negative pressure is placed so that the drug solution L1 stored in the body unit 3 does not leak out from the inlet port 31 or the ejection port 35. However, a configuration in which a self-sealing valve or the like is provided in place of the urethane foam, or the like may be adopted.

In the mounting portion 37, a support portion 36 that supports the actuator holder 21 in an abutting state when mounting the actuator unit 2 is formed. Then, in a portion for mounting the actuator unit 2 of the mounting portion 37, a displacement magnification mechanism 40 having a first wall portion 41, a second wall portion 42, and a liquid chamber 43, which is sandwiched between the first wall portion 41 and the second wall portion 42 in the Z-axis direction, and in which a liquid L2 is enclosed is provided.

Figure 2:
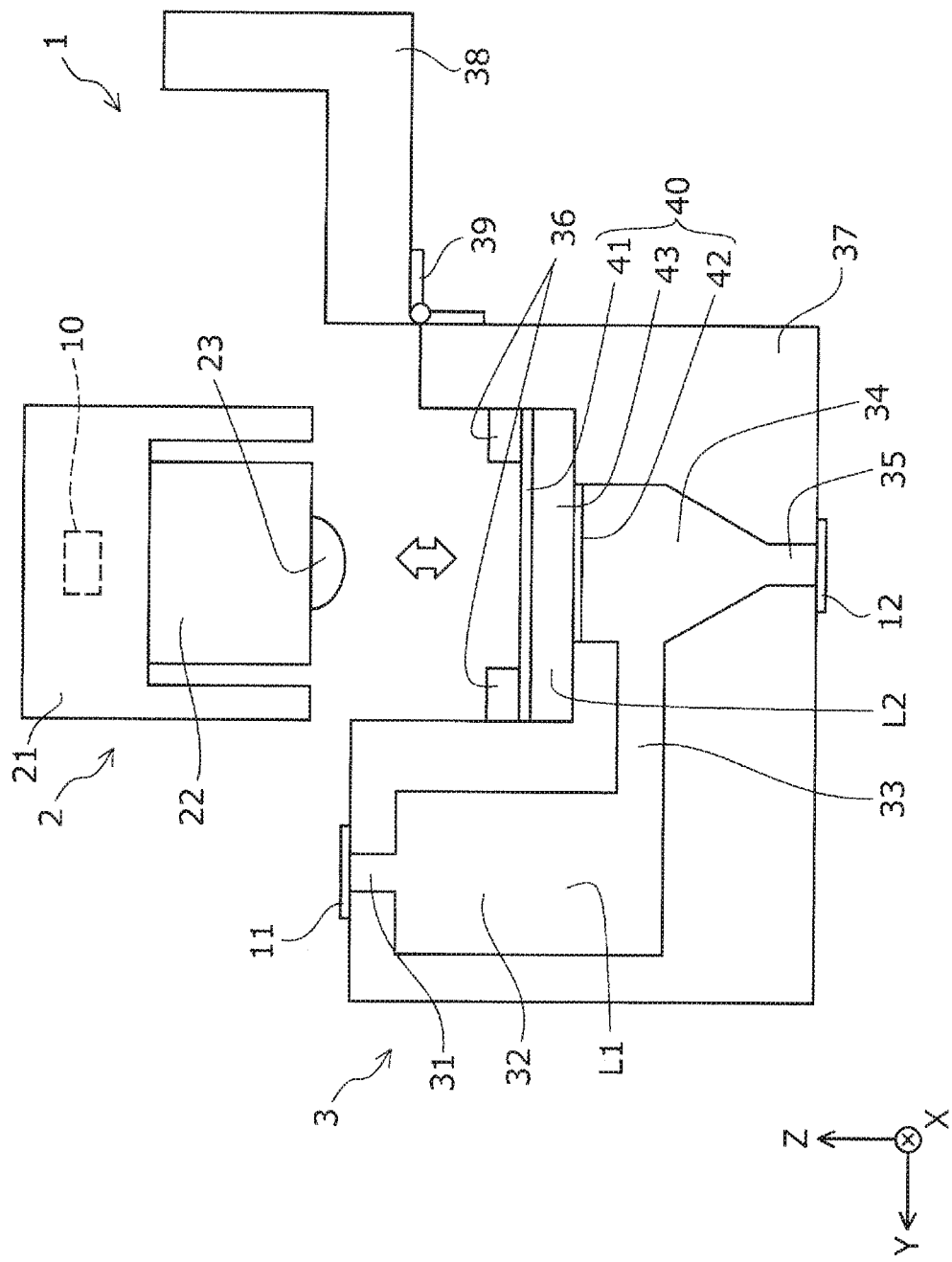
FIG. 2 is a schematic view showing the drug solution administration unit of the first embodiment, and is a view showing a state where the actuator unit is detached from the body portion.

Further, as shown in FIGS. 1 and 2, the drug solution administration unit 1 of this embodiment is configured to be able to attach a seal portion 11 that closes the inlet port 31 and a seal portion 12 that closes the ejection port 35 when a user does not use the drug solution administration unit 1.

Figure 3:
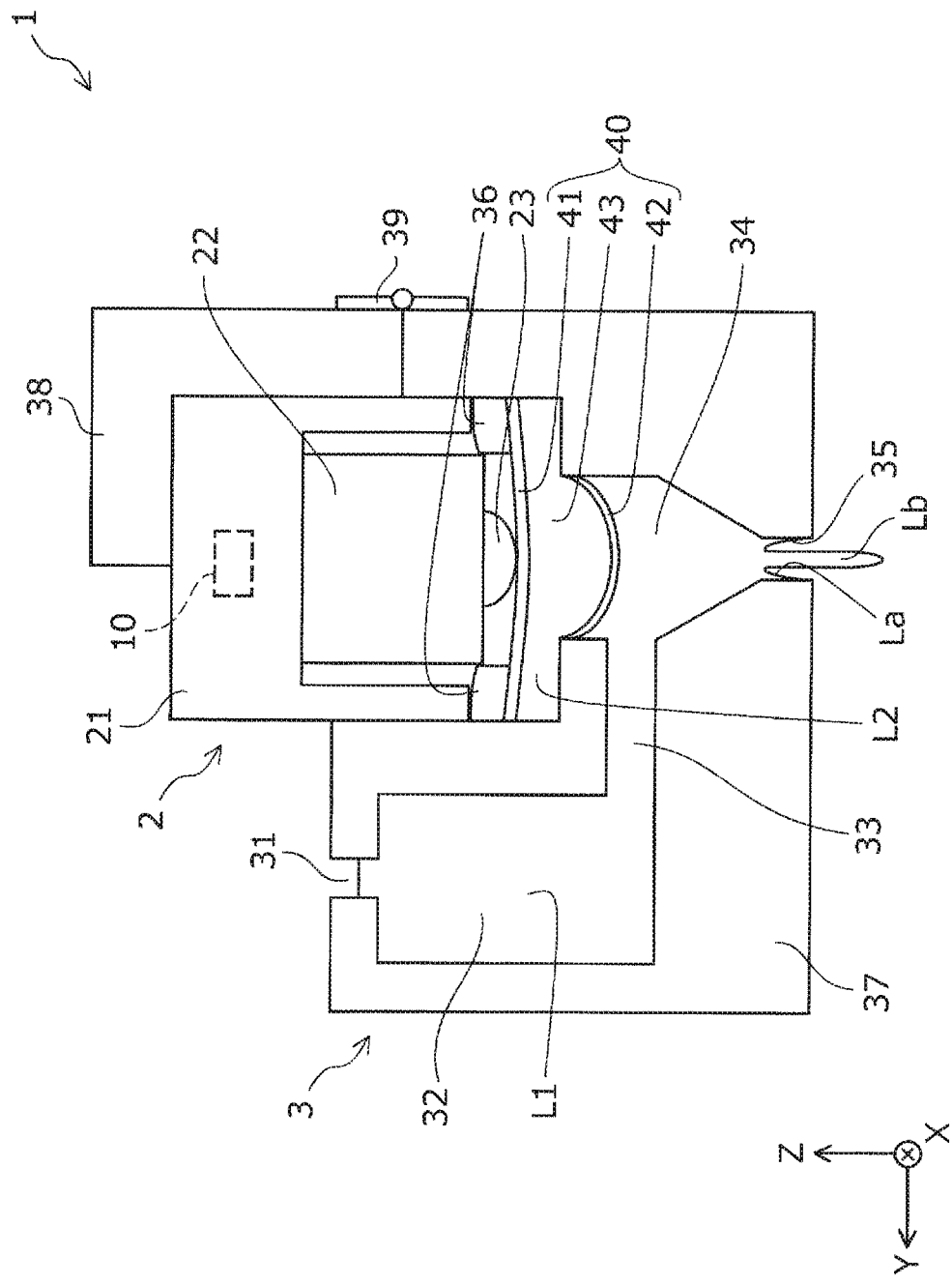
FIG. 3 is a schematic view showing the drug solution administration unit of the first embodiment, and is a view showing a state where the actuator unit is driven.
Figure 4:
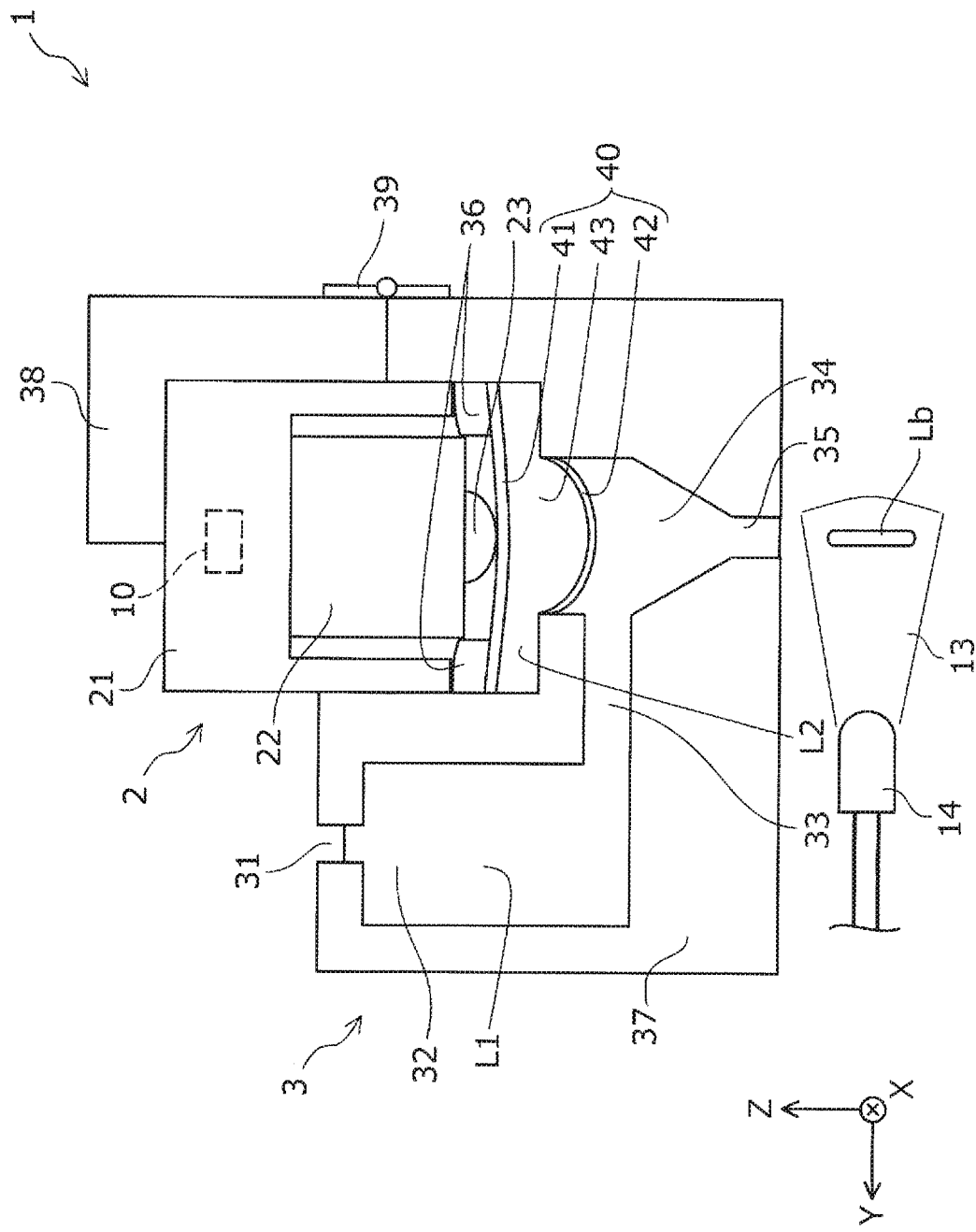
FIG. 4 is a view showing a state where an ejection rate of a drug solution is visually measured using the drug solution administration unit of the first embodiment.

However, as shown in FIGS. 3 and 4, when a user uses the drug solution administration unit 1, the seal portion 11 and the seal portion 12 are detached.

Here, as shown in FIGS. 1 to 4, the drug solution administration unit 1 of this embodiment is configured to include one actuator unit 2 and one ejection port 35. However, it is not limited to such a configuration, and for example, a configuration in which the drug solution administration unit 1 includes a plurality of actuator units 2, one pressure chamber 34 to be used in common for the plurality of actuator units 2, and one ejection port 35 that communicates with the pressure chamber 34, or the like may be adopted. By adopting such a configuration, fine adjustment of the ejection amount of the drug solution L1 from the ejection port 35 is facilitated. However, even if the drug solution administration unit 1 is configured to include one actuator unit 2 and one ejection port 35 as in this embodiment, by continuously driving the actuator 22 a plurality of times, the ejection amount of the drug solution L1 from the ejection port 35 can be adjusted.

The drug solution administration unit 1 of this embodiment is configured to include the actuator unit 2 and eject the drug solution L1 from the ejection port 35 by driving the actuator 22 of the actuator unit 2. However, it is not limited to such a configuration. For example, an ejection portion configured to include a piston inside a nozzle having a tip with a tapered shape is used, and a so-called jet dispenser-type ejection portion that ejects the drug solution L1 while allowing the piston to collide with the tapered portion may be used. However, a configuration in which a contactless ejection portion like the drug solution administration unit of this embodiment is used is preferred because the exchangeability is favorable and also the occurrence of impurities involved in the collision of the members can be suppressed. In the present disclosure, the jet dispenser-type ejection portion shall also be included the inkjet head.

According to the type of the target site, the state of the target site, or the like, various materials can be used as the drug solution L1 without limitation. For example, other than a material constituted only by a liquid, a material containing a solid drug to be dissolved at body temperature, a material containing a solid to be used for a purpose other than treatment such as a pigment, or the like can also be used as the drug solution L1. As an inclusion that can be used as the drug solution L1, for example, water, a moisturizer, hyaluronic acid, an isotonic agent, a vaccine, serum, insulin, vitamins, an antimicrobial agent, a coloring material, a dye, a preservative, an antiallergic agent, an anticancer agent, an antihistamine, an antibiotic agent, an antipsychotic drug, narcotic drugs, an anticholinergic drug, a hair agent, oils, and the like can be used alone or in combination. In particular, it is desirable to use an inclusion having a molecular weight of about 500 or more that cannot penetrate the corneum. Further, in order to promote transdermal administration, an alcohol such as ethanol, propylene glycol, or menthol can also be used. In addition, aside from the ejection of the drug solution L1 from the ejection port 35, water or the like is sprayed from a place other than the ejection port 35 so as to moisturize a target site, and for example, the corneal water content is set to 15% or more, and thereafter, the drug solution L1 may be ejected.

As shown in FIGS. 1, 3, and 4, in a state where the actuator unit 2 is mounted on the mounting portion 37, the abutment portion 23 is in a state of being in contact with the first wall portion 41. The first wall portion 41 and the second wall portion 42 are both constituted by a flexible member. Then, the area of the second wall portion 42 is smaller than the area of the first wall portion 41. As shown in FIGS. 3 and 4, when the first wall portion 41 is pressed by the abutment portion 23, the first wall portion 41 is deflected downward in the drawing, and since the liquid L2 is enclosed in the liquid chamber 43, the second wall portion 42 is also deflected downward in the drawing. Here, the area of the second wall portion 42 is smaller than the area of the first wall portion 41, and therefore, the deflection amount in a direction along the Z-axis direction of the second wall portion 42 becomes larger than the deflection amount in a direction along the Z-axis direction of the first wall portion 41. Therefore, the displacement magnification mechanism 40 is configured to be able to magnify the displacement of the actuator 22 and transmit the displacement to the pressure chamber 34.

The drug solution administration unit 1 of this embodiment is configured to be able to move the abutment portion 23 not only downward in the drawing but also upward in the drawing by driving the actuator 22. Then, the first wall portion 41 can be deflected upward in accordance with the upward movement of the abutment portion 23. When the first wall portion 41 is deflected upward, the second wall portion 42 is also deflected upward. Since the drug solution administration unit 1 of this embodiment is configured in this manner, not only can a positive pressure be generated in the pressure chamber 34 by applying a pressure to the pressure chamber 34, but also a negative pressure can be generated in the pressure chamber 34. As a configuration in which a negative pressure can also be generated in the pressure chamber 34, a configuration in which the abutment portion 23 is adhered to the first wall portion 41 so that also the first wall portion 41 moves in the Z-axis direction with the movement in the Z-axis direction of the abutment portion 23 can also be adopted, but a configuration in which a force is applied upward in advance so that the first wall portion 41 is biased toward the abutment portion 23 may be adopted.

Therefore, the drug solution administration unit 1 of this embodiment can eject the drug solution L1 from the ejection port 35 by repeating a state where a positive or negative pressure is not applied to the pressure chamber 34 and a state where a positive pressure is applied to the pressure chamber 34. Further, by repeating an operation of generating a negative pressure in the pressure chamber 34 and an operation of generating a positive pressure in the pressure chamber 34, a recessed shape La is formed at the surface of the drug solution L1 at the ejection port 35, and thereafter, a columnar shape Lb is formed from a part of the recessed shape La as shown in FIG. 3, and the drug solution L1 in the columnar shape Lb can be ejected from the ejection port 35 as shown in FIG. 4.

The ejection rate of the drug solution L1 can be visually confirmed by ejecting the drug solution L1 in the columnar shape Lb from the ejection port 35, and for example as shown in FIG. 4, emitting strobe light 13 at a predetermined timing from the moment when the actuator 22 is driven corresponding to the moment when the drug solution L1 is ejected from the ejection port 35 using a stroboscope having a light 14 or the like. Specifically, for example, a scale with graduations or the like is located in the vicinity of the ejection port 35, and the strobe light 13 is emitted after a predetermined time from the moment when the actuator 22 is driven, whereby the ejection rate of the drug solution L1 can be visually confirmed. This is because the drug solution L1 ejected from the ejection port 35 is in the columnar shape Lb, and therefore is easily visually recognized. For example, when the strobe light 13 is emitted after 0.001 s from the moment when the actuator 22 is driven and the tip in the ejection direction of the drug solution L1 starts to be ejected from the ejection port 35, if the tip in the ejection direction of the drug solution L1 is located at a position separated by a distance of 5 cm from the ejection port 35, the ejection rate is 5 cm/0.001 s, that is, 50 m/s. Since the ejection rate of the drug solution L1 can be visually confirmed, the ejection rate can be confirmed with a simple device configuration.

However, the ejection rate of the drug solution L1 may be confirmed not visually, but by using a camera capable of capturing an image of the drug solution L1 to be ejected from the ejection port 35 or the like. This is because by using a camera capable of capturing an image of the drug solution L1 to be ejected from the ejection port 35 or the like, the ejection rate can be accurately confirmed. Further, since the camera can also be diverted to a camera for capturing an image of the target site, it is also possible to eject the drug solution L1 at an accurate position.

Figure 5:
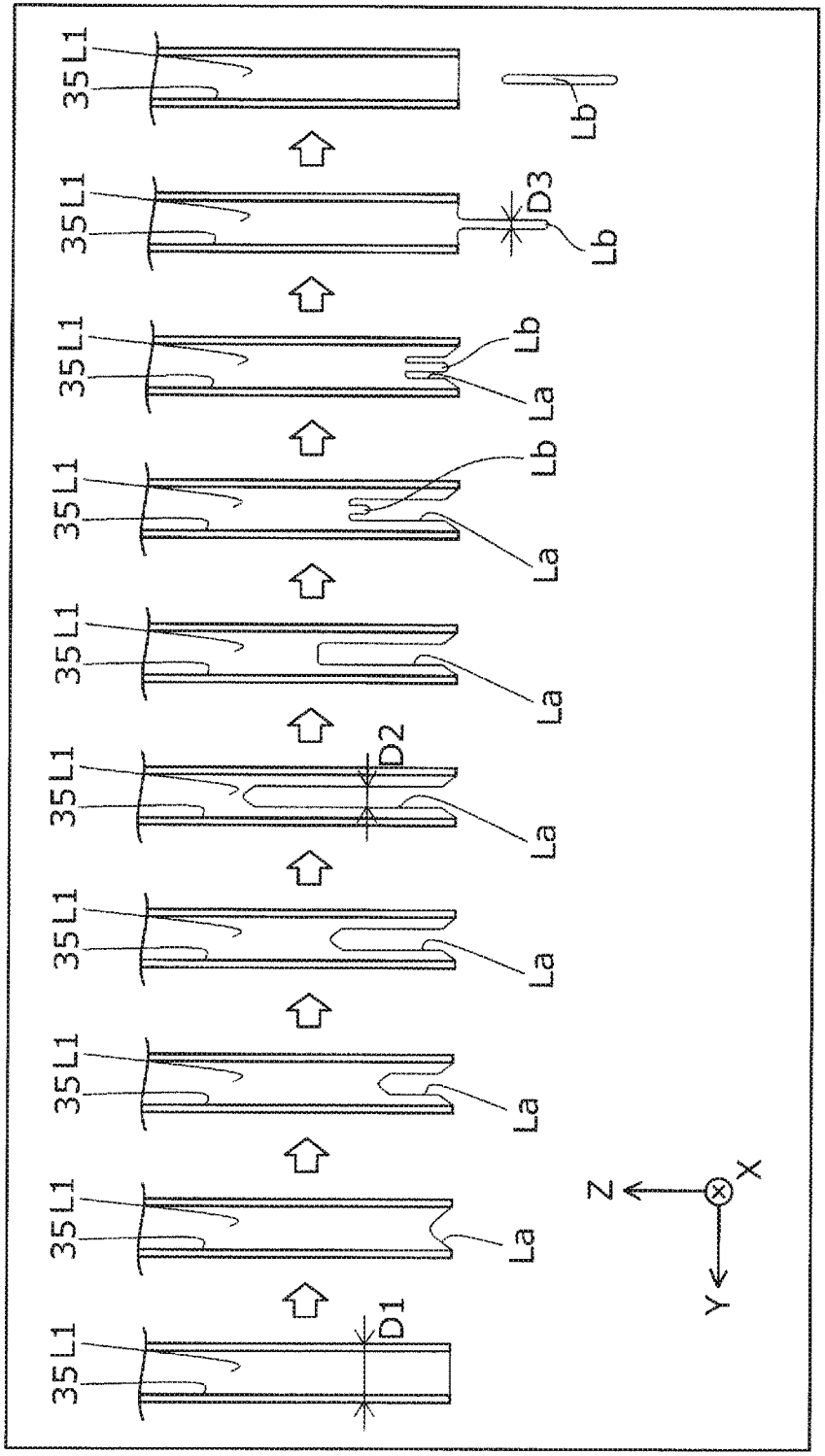
FIG. 5 is a view showing a state of the inside of an ejection port when a drug solution is ejected in the drug solution administration unit of the first embodiment.

Next, in the drug solution administration unit 1 of this embodiment, an operation in which the recessed shape La is formed at the surface of the drug solution L1 at the ejection port 35, and thereafter, the columnar shape Lb is formed from a part of the recessed shape La, and the drug solution L1 in the columnar shape Lb is ejected from the ejection port 35 will be described with reference to FIG. 5.

When the drug solution L1 is ejected from the ejection port 35, first, the actuator 22 is driven so as to move the abutment portion 23 upward and deflect the first wall portion 41 upward. Then, a negative pressure is generated in the liquid chamber 43, and therefore, the second wall portion 42 is also deflected upward. By the upward deflection of the second wall portion 42, a negative pressure is generated in the pressure chamber 34, and the recessed shape La is formed at the surface of the drug solution L1 at the ejection port 35. The leftmost state to the fifth state from the left in FIG. 5 show a manner in which the recessed shape La is formed at the surface of the drug solution L1 at the ejection port 35 by the upward deflection of the second wall portion 42. The depth at which the recessed shape La is formed in the Z-axis direction is not particularly limited, but preferably has a length three times or more larger than an inner diameter D1 of the ejection port 35 in order to make the ejection rate of the drug solution L1 high.

Subsequently, the actuator 22 is driven so as to move the abutment portion 23 downward and deflect the first wall portion 41 downward. Then, a positive pressure is generated in the liquid chamber 43, and therefore, the second wall portion 42 is also deflected downward. By the downward deflection of the second wall portion 42, a positive pressure is generated in the pressure chamber 34, and the columnar shape Lb is formed along the Z-axis direction at a central portion of the recessed shape La formed at the surface of the drug solution L1 at the ejection port 35. Then, the columnar shape Lb grows downward, and when it has grown to a desired length, the columnar shape Lb is cut off from the surface of the drug solution L1, and the drug solution L1 is ejected in a state where the columnar shape Lb is maintained. The sixth state from the left to the rightmost state in FIG. 5 show a manner in which the columnar shape Lb is formed at the surface of the drug solution L1 at the ejection port 35, and the drug solution L1 in the columnar shape Lb is ejected by the downward deflection of the second wall portion 42.

When viewed from the Z-axis direction, an inner diameter D2 of the recessed shape La with respect to the inner diameter D1 of the ejection port 35 is about ⅔ times, and a diameter D3 of the columnar shape Lb with respect to the inner diameter D2 is about ⅓ times. The drug solution administration unit 1 of this embodiment can eject the drug solution L1 from the ejection port 35 so that the diameter D3 is 20 μm or more and 200 μm or less and the ejection rate of the drug solution L1 when it is ejected from the ejection port 35 is 30 m/s or more. The inkjet device configured to include the actuator 22 and the displacement magnification mechanism 40 as described with reference to FIGS. 1 to 4 can eject the drug solution L1 at a high rate such that the ejection rate is 30 m/s or more.

As summarized here, the drug solution administration unit 1 of this embodiment is an inkjet device including the actuator unit 2 and the body unit 3 as the inkjet head that ejects the drug solution L1, and the controller 10 that controls the ejection of the drug solution L1 from the inkjet head. Then, a drug solution administration method in which the drug solution L1 is made to pierce a target site and is administered to the target site can be implemented by ejecting the drug solution L1 from the ejection port 35 so that the diameter D3 of the drug solution L1 when it is ejected from the ejection port 35 is 20 μm or more and 200 μm or less and the ejection rate of the drug solution L1 when it is ejected from the ejection port 35 is 30 m/s or more using the drug solution administration unit 1.

In this manner, by administering the drug solution L1 to the target site under the conditions that the drug solution L1 is ejected so that the diameter D3 is 20 μm or more and 200 μm or less and the ejection rate is 30 m/s or more, the drug solution L1 can be administered while piercing the surface of the target site without causing a patient to feel pain, and the drug solution L1 can be made to sufficiently penetrate into the target site. Further, by ejecting the drug solution L1 from the inkjet head, the drug solution L1 can be administered to the target site without bringing the other constituent members such as a needle into contact with the target site, and thus, the adverse effect can also be suppressed. Note that the "target site" represents an affected area or the like to which the drug solution is desired to be administered such as a skin of a human body tissue or an organ such as an eye, a heart, a lung, a liver, or a stomach, or a skin, an organ, or the like of an animal other than a human. Further, the "diameter" as used herein is a diameter when viewed from a direction along the Z-axis direction as described above, in other words, the ejection direction of the drug solution L1.

Here, the actuator unit 2 and the body unit 3 as the inkjet head have the ejection port 35 that ejects the drug solution L1, the pressure chamber 34 that communicates with the ejection port 35, the actuator 22 that is displaced in a pressing direction corresponding to the downward direction in FIGS. 1 to 4 and in an opposite direction to the pressing direction corresponding to the upward direction in FIG. 4, and the displacement magnification mechanism 40 that magnifies the amount of displacement and transmits the displacement of the actuator 22 to the pressure chamber 34. It is difficult to eject the drug solution L1 so that the ejection rate is 30 m/s or more using a general inkjet head. However, the drug solution administration unit 1 of this embodiment can press the pressure chamber 34 with a larger amount of displacement than the amount of displacement of the actuator 22 due to the displacement magnification mechanism 40 as described above, and therefore, the drug solution L1 can be ejected so that the ejection rate is 30 m/s or more.

Further, the displacement magnification mechanism 40 includes the liquid chamber 43 in which the liquid L2 is enclosed. In addition, the displacement magnification mechanism 40 includes the first wall portion 41 that constitutes a part of a wall face of the liquid chamber 43, and that is displaced according to the displacement of the actuator 22 so as to apply a pressure to the liquid L2. Further, the displacement magnification mechanism 40 includes the second wall portion 42 that constitutes a part of a wall face of the liquid chamber 43, that has a smaller area facing the liquid L2 than the area of the first wall portion 41 facing the liquid L2, and that is displaced in the pressing direction in a state where an elastic force acting in the opposite direction to the pressing direction is generated by a pressure of the liquid L2 when a pressure is applied to the liquid L2 by the displacement of the first wall portion 41. That is, by adopting a configuration in which the displacement magnification mechanism 40 is provided with the liquid chamber 43 having the first wall portion 41 and the second wall portion 42, the high-precision displacement magnification mechanism can be constituted. Then, by the high-precision displacement magnification mechanism 40, the drug solution L1 can be ejected so that the ejection rate is 30 m/s or more with high precision.

Further, as described above, under the control of the controller 10, the surface of the drug solution L1 formed at the ejection port 35 is drawn toward the inside of the pressure chamber 34 so as to form the recessed shape La by displacing the actuator 22 in the opposite direction to the pressing direction. Then, by displacing the actuator 22 in the pressing direction thereafter, the columnar shape Lb protruding toward the outside of the pressure chamber 34 is formed at a central portion when viewed from the ejection direction of the drug solution L1 at the surface in the recessed shape La and also the drug solution L1 in the columnar shape Lb can be ejected. In this manner, by displacing the actuator 22 so as to once recess the surface of the drug solution L1 formed at the ejection port 35, and thereafter form the columnar shape Lb at the central portion of the recessed portion, the drug solution L1 can be ejected so that the ejection rate is 30 m/s or more with high precision. Further, when the drug solution L1 is ejected in a spherical shape, it is difficult to visually confirm whether or not the drug solution L1 is ejected, however, by ejecting the drug solution L1 in the columnar shape Lb, it is possible to visually confirm whether or not the drug solution L1 is ejected.

However, the ejection method is not limited to the ejection method as described above. The actuator 22 may be displaced in the pressing direction from the beginning without displacing the actuator 22 in the opposite direction to the pressing direction under the control of the controller 10. According to the configuration in which the displacement magnification mechanism 40 is included, even if such an ejection method is adopted, the drug solution L1 can be ejected so that the ejection rate is 30 m/s or more.

The drug solution administration unit 1 of this embodiment includes a stroboscope having the light 14 or the like as the ejection rate measurement unit for the drug solution L1. Then, a user can perform administration of the drug solution L1 after measuring the ejection rate of the drug solution L1. The dose is sometimes restricted according to the type of the drug solution L1 to be used, however, by implementing the drug solution administration method using the drug solution administration unit 1 of this embodiment, the drug solution L1 can be administered after adjusting the conditions so that the drug solution L1 can pierce the target site.

The inkjet head of the drug solution administration unit 1 of this embodiment can change the number of times of ejection of the drug solution L1 at the same position of the target site from one time to a plurality of times by, for example, continuously performing an ejection operation under the control of the controller 10. By changing the number of times of ejection of the drug solution L1, the drug solution L1 can be administered while adjusting the penetration depth of the drug solution L1 into the target site. A preferred penetration depth of the drug solution L1 into the target site varies depending on the state of the target site, the type of the drug solution L1 to be used, or the like. If the number of times of ejection of the drug solution L1 at the same position of the target site is increased by continuously performing the ejection operation a plurality of times, the penetration depth of the drug solution L1 into the target site is increased. By using the drug solution administration unit 1 of this embodiment, the drug solution L1 can be administered while adjusting the penetration depth of the drug solution L1 into the target site by a simple method in which the number of times of ejection of the drug solution L1 at the same position of the target site is changed.

The inkjet head of the drug solution administration unit 1 of this embodiment is configured to be able to eject the drug solution L1 with a plurality of ejection diameters under the control of the controller 10. Specifically, it is configured to be able to eject the drug solution L1 with a plurality of ejection diameters by adjusting the amount of displacement in a direction along the Z-axis direction of the actuator 22 or by continuously displacing the actuator 22 at a high rate. By changing the ejection diameter of the drug solution L1 under the control of the controller 10, the drug solution L1 can be administered while adjusting the application range of the drug solution L1 to the local target site. By narrowing the ejection diameter of the drug solution L1, the application range of the drug solution L1 to the local target site can be adjusted to an extremely small range. By using the drug solution administration unit 1 of this embodiment, the drug solution L1 can be administered while adjusting the application range of the drug solution L1 to the local target site by changing the ejection diameter of the drug solution L1. Note that the ejection diameter of the drug solution L1 corresponds to the above-mentioned diameter D3.

The inkjet head of the drug solution administration unit 1 of this embodiment is configured to be able to eject the drug solution L1 at a plurality of ejection rates under the control of the controller 10. Specifically, it is configured to be able to eject the drug solution L1 at a plurality of ejection rates by adjusting the amount of displacement in a direction along the Z-axis direction of the actuator 22 or the rate of displacement of the actuator 22. The drug solution L1 can be administered while adjusting the penetration depth of the drug solution L1 into the target site by changing the ejection rate of the drug solution L1 under the control of the controller 10. By increasing the ejection rate of the drug solution L1, the penetration depth of the drug solution L1 into the target site is increased. By using the drug solution administration unit 1 of this embodiment and changing the ejection rate of the drug solution L1, the drug solution L1 can be administered while adjusting the penetration depth of the drug solution L1 into the target site.

The drug solution administration unit 1 of this embodiment is a handy type, and a desired amount of the drug solution L1 can be administered to the target site by a user holding it with a hand. However, it is also possible to administer the drug solution L1 to the target site by mounting the drug solution administration unit 1 of this embodiment on a moving mechanism for moving the drug solution administration unit 1 to a desired position. In other words, the inkjet device includes a moving mechanism for changing the position of the drug solution administration unit 1, and in the administration of the drug solution L1, the drug solution L1 can also be administered while changing the position of the inkjet head that is the ejection portion of the drug solution administration unit 1 by the moving mechanism. Therefore, when the target site is located over a wide area, or the like, the drug solution L1 can be easily administered at a preferred position. Further, for example, when the drug solution L1 is administered to a site from the elbow to the wrist, or the like, the drug solution L1 shall be administered to a region where the hardness of the skin that is the target site varies, however, the drug solution L1 can be administered over a wide area while changing the number of times of ejection, the ejection rate, or the like according to the hardness of the skin. Note that the inkjet device preferably includes an indentometer capable of measuring the hardness of the skin.

Here, the moving mechanism may be configured to also move a constituent member other than the inkjet head together therewith as long as it is configured to be able to move at least the inkjet head that is the ejection portion of the drug solution administration unit 1. Further, the moving mechanism may be configured to one-dimensionally move (reciprocally move) the inkjet head continuously or intermittently, and other than this, it may also be configured to two-dimensionally or three-dimensionally move the inkjet head continuously or intermittently.

Second Embodiment

Next, a drug solution administration unit 1 of a second embodiment will be described with referent to FIG. 6. FIG. 6 is a view corresponding to FIG. 2 for the drug solution administration unit 1 of the first embodiment, and also in FIG. 6, the constituent members common to those in the first embodiment are denoted by the same reference numerals, and a detailed description thereof will be omitted. Here, the drug solution administration unit 1 of this embodiment has the same characteristics as those of the drug solution administration unit 1 of the first embodiment described above, and also has the same form as that of the drug solution administration unit 1 of the first embodiment except for the parts described below.

As shown in FIG. 6, the drug solution administration unit 1 of this embodiment includes a body unit 3 and a control unit 5 having a controller 10 and a power supply (not shown) or the like. The actuator 22 is provided in the body unit 3. The control unit 5 can be moved in the arrow direction in FIG. 6 with respect to the body unit 3, and is configured to be attachable to and detachable from the body unit 3.

As shown by the drug solution administration units 1 of the first embodiment and the second embodiment, part of the constituent members can be configured to be attachable to and detachable from the body unit 3. The actuator unit 2 may be configured to be attachable to and detachable from the body unit 3 or the control unit 5 may be configured to be attachable to and detachable from the body unit 3, and other than these, a drug solution tank that stores the drug solution L1 may be configured to be attachable and detachable, a power supply unit may be configured to be attachable and detachable, and so on. By adopting a configuration in which part of the constituent members are attachable to and detachable from the body unit 3 in this manner, a specification can be made capable of easily replacing part of the constituent members. Then, for example, by storing management information such as the date of expiry in the attachable and detachable constituent members, for example, an old drug solution L1 is prevented from being used, and so on, and thus, the drug solution administration unit 1 can be managed with high precision.

Third Embodiment

Next, a drug solution administration unit 1 of a third embodiment will be described with referent to FIG. 7. FIG. 7 is a view corresponding to FIG. 1 for the drug solution administration unit 1 of the first embodiment, and also in FIG. 7, the constituent members common to those in the first embodiment and the second embodiment are denoted by the same reference numerals, and a detailed description thereof will be omitted. Here, the drug solution administration unit 1 of this embodiment has the same characteristics as those of the drug solution administration unit 1 of the first embodiment described above, and also has the same form as that of the drug solution administration unit 1 of the first embodiment except for the parts described below.

As shown in FIG. 7, the drug solution administration unit 1 of this embodiment is provided with a spacer 15 in a cylindrical shape surrounding the circumference of the ejection port 35. The drug solution administration unit 1 of this embodiment has exactly the same configuration as the drug solution administration unit 1 of the first embodiment except that the spacer 15 is provided. The spacer 15 of this embodiment is configured to be stretchable in the ejection direction along the Z-axis direction, and is configured to be able to adjust the length in the ejection direction from the ejection port 35 within a range of 5 mm or more and 20 mm or less.

That is, the drug solution administration unit 1 of this embodiment includes the spacer 15 as an ejection distance specifying unit that specifies the ejection distance of the drug solution L1, which is a distance from the ejection port 35 to the target site, and by specifying the ejection distance with the spacer 15, the administration of the drug solution L1 is made possible within a range where the ejection distance is 5 mm or more and 20 mm or less. If the ejection distance is too short, the drug solution L1 may bounce back to the inkjet head of the drug solution administration unit 1 to contaminate the drug solution administration unit 1 and make it unhygienic, and if the ejection distance is too long, it may become difficult for the drug solution L1 to reach the target site at a desired ejection rate. By administering the drug solution L1 using the drug solution administration unit 1 of this embodiment, the administration of the drug solution L1 can be performed within a range where the ejection distance is 5 mm or more and 20 mm or less. Therefore, the inkjet head can be prevented from being contaminated and becoming unhygienic, or the drug solution L1 can be prevented from not reaching the target site at a desired ejection rate.

The present disclosure is not limited to the above-mentioned embodiments, but can be realized in various configurations without departing from the gist of the present disclosure. The technical features in the embodiments corresponding to the technical features in the respective forms described in "SUMMARY" of the present disclosure may be appropriately replaced or combined in order to solve part or all of the problems described above or achieve part or all of the advantageous effects described above. Further, the technical features may be appropriately deleted unless they are described as essential features in the specification.

What is claimed is:

1. A drug solution administration method using an inkjet device including an inkjet head that ejects a drug solution from an ejection port, and a controller that controls the ejection of the drug solution from the inkjet head, wherein
    the drug solution is made to pierce a target site and is administered to the target site by ejecting the drug solution from the inkjet head so that a diameter of the drug solution when it is ejected from the inkjet head is 20 μm or more and 200 μm or less and an ejection rate of the drug solution when the drug solution is ejected from the inkjet head is 30 m/s or more under control of the controller, wherein
    under the control of the controller
        a surface of the drug solution formed at the ejection port is drawn toward a pressure chamber of the inkjet head so as to form a recessed shape of the drug solution, and
        a columnar shape of the drug solution, protruding toward an outside of the pressure chamber, is formed at a central portion at the surface in the recessed shape when viewed from an ejection direction of the drug solution and also the drug solution in the columnar shape is ejected from the ejection port, and
    the inkjet head comprises:
        an ejection port for ejecting the drug solution,
        a pressure chamber that communicates with the ejection port,
        an actuator that is displaced in a pressing direction and in an opposite direction to the pressing direction, and
        a displacement magnification mechanism for magnifying an amount of displacement and transmitting the displacement of the actuator to the pressure chamber, the displacement magnification mechanism comprising a liquid chamber enclosing a liquid different from the drug solution elected from the election port.

2. The drug solution administration method according to claim 1, wherein
    the inkjet device includes an ejection rate measurement unit for measuring an ejection rate of the drug solution prior to delivery to the target site, and
    the administration of the drug solution to the target site is performed after measuring the ejection rate of the drug solution.

3. The drug solution administration method according to claim 1, wherein
    the drug solution is administered while adjusting a penetration depth of the drug solution into the target site by changing a number of times of ejection of the drug solution at a same position of the target site under the control of the controller.

4. The drug solution administration method according to claim 1, wherein
    the inkjet device includes a moving mechanism for changing a position of the inkjet head, and
    in the administration of the drug solution, the drug solution is administered while changing the position of the inkjet head by the moving mechanism.

5. The drug solution administration method according to claim 1, wherein
    the inkjet head is configured to be able to eject the drug solution with a plurality of ejection diameters under the control of the controller, and
    the drug solution is administered while adjusting an application range of the drug solution to a local target site by changing the ejection diameter of the drug solution under the control of the controller.

6. The drug solution administration method according to claim 1, wherein the inkjet head is configured to be able to eject the drug solution at a plurality of ejection rates under the control of the controller, and the drug solution is administered while adjusting a penetration depth of the drug solution into the target site by changing the ejection rate of the drug solution under the control of the controller.

7. The drug solution administration method according to claim 1, wherein the inkjet device includes an ejection distance specifying unit that specifies an ejection distance of the drug solution, which is a distance from the inkjet head to the target site, and the administration of the drug solution is performed within a range where the ejection distance is 5 mm or more and 20 mm or less by specifying the ejection distance by the ejection distance specifying unit.

8. The drug solution administration method according to claim 1, wherein the displacement magnification mechanism includes a first wall portion that constitutes a part of a wall face of the liquid chamber, and that is displaced according to the displacement of the actuator so as to apply a pressure to the liquid, and a second wall portion that constitutes a part of a wall face of the liquid chamber, that has a smaller area facing the liquid than the area of the first wall portion facing the liquid, and that is displaced in the pressing direction in a state where an elastic force acting in an opposite direction is generated by a pressure of the liquid when the pressure is applied to the liquid by the displacement of the first wall portion.

9. The drug solution administration method according to claim 1, wherein under the control of the controller, the columnar shape protruding toward the outside of the pressure chamber is formed at the central portion when viewed from the ejection direction of the drug solution at the surface in the recessed shape and also the drug solution in the columnar shape is ejected by displacing the actuator in the pressing direction.

* * * * *